United States Patent [19]

Brois et al.

[11] 4,116,876

[45] Sep. 26, 1978

[54] BORATED OXAZOLINES AS VARNISH INHIBITING DISPERSANTS IN LUBRICATING OILS

[75] Inventors: Stanley J. Brois, Westfield; Antonio Gutierrez, Hamilton Square; Esther D. Winans, Colonia, all of N.J.

[73] Assignee: Exxon Research & Engineering Co., Linden, N.J.

[21] Appl. No.: 763,545

[22] Filed: Jan. 28, 1977

[51] Int. Cl.$^2$ .......................... C10M 1/10; C10M 1/50
[52] U.S. Cl. .............................. 252/49.6; 260/307 R; 260/307 A
[58] Field of Search .................... 252/49.6; 260/307 R, 260/307 A

[56] References Cited

U.S. PATENT DOCUMENTS

| | | | |
|---|---|---|---|
| 3,254,025 | 5/1966 | LeSuer | 252/32.7 |
| 3,389,124 | 6/1968 | Sparks | 252/49.6 X |
| 3,446,808 | 5/1969 | Cyba | 252/49.6 X |
| 3,505,226 | 4/1970 | Cyba | 252/49.6 |
| 4,035,309 | 7/1977 | Brois | 252/49.6 UX |

FOREIGN PATENT DOCUMENTS

| | | | |
|---|---|---|---|
| 2,534,921 | 2/1976 | Fed. Rep. of Germany | 252/49.6 UX |
| 2,534,922 | 2/1976 | Fed. Rep. of Germany | 252/49.6 UX |
| 1,444,904 | 2/1969 | Fed. Rep. of Germany | 252/49.6 UX |

*Primary Examiner*—Paul F. Shaver
*Attorney, Agent, or Firm*—Roland A. Dexter; Frank T. Johmann

[57] ABSTRACT

Borated derivatives of: (a) hydrocarbyl substituted mono- and bis-oxazolines obtained as a reaction product of hydrocarbyl substituted dicarboxylic acid, ester, or anhydride, for example, polyisobutenylsuccinic anhydride with from 1 to 2 molar equivalents of a 2,2-disubstituted-2-amino-1-alkanols, such as tris-(hydroxymethylamino)methane (THAM); and, (b) lactone oxazolines obtained as a reaction product of hydrocarbyl substituted lactone carboxylic acids, for example, polybutyl lactone carboxylic acid, with 2,2-disubstituted-2-amino-1-alkanols, such as tris-(hydroxymethyl)aminomethane (THAM), and their derivatives are useful additives in lubricating oils since both the sludge dispersant and/or varnish inhibiting properties of said oil are enhanced.

17 Claims, No Drawings

BORATED OXAZOLINES AS VARNISH INHIBITING DISPERSANTS IN LUBRICATING OILS

BACKGROUND OF THE INVENTION

The present invention concerns hydrocarbon soluble borated derivatives of oxazolines, their method of preparation, and the utility of said borated oxazolines as lubricating oil additives, which markedly improve the sludge dispersancy-varnish inhibiting properties of lubricating oils employed for crankcase lubrication of internal combustion engines.

There are two principal environments which are encountered by automotive crankcase lubricants, i.e. cyclical high and low temperatures from stop-and-go driving and continuous high temperatures from extended operation of the automobile over long distances. Each of these environments provokes the presence in the lubricant of varying proportions of foreign particles such as dirt, soot, water and decomposition products resulting from breakdown of the oil. This foreign matter appears responsible for the deposition of a mayonnaise-like sludge which circulates with the oil.

Besides sludge formation, the inner surfaces tend to develop a varnish deposit which results from the operation of the engine at continuous high temperatures. In such an environment, oil breakdown results in the formation of acidic materials which in themselves corrode the metal surfaces of the bearings, pistons, etc., as well as catalyze the decomposition of the lubricating oil which decomposition is manifested in hard, carbonaceous deposits which accumulate in the piston ring groove and form a varnish on the piston skirts and other metal surfaces.

During the past decade, ashless sludge dispersants have become increasingly important, primarily in improving the performance of lubricants in keeping the engine clean of deposits and permitting extended crankcase oil drain periods while avoiding the undesirable environmental impact of the earlier used metal-containing additives. Most commercial ashless dispersants fall into several general categories. In one category, an amine or polyamine is attached to a long-chain hydrocarbon polymer (the oil solubilizing portion of the molecule), usually polyisobutylene through an acid group, such as a monocarboxylic acid, for example, see U.S. Pat. No. 3,444,170 or a dicarboxylic acid material such as polyisobutenyl succinic anhydride, by forming amide or imide linkages such as described in U.S. Pat. Nos. 3,172,892 and 3,272,746 and may include the reaction product of such materials with boron (see U.S. Pat. Nos. 3,087,936 and 3,254,025) generally forming a mixed boric acid salt which is hydrolytically rather unstable reducing its usefulness.

Reaction products of acylated nitrogen intermediates (from the reaction of an alkenyl succinic acid producing compound and a hydroxy hydrocarbon amine) and a boron compound are taught as additives for lubricants in U.S. Pat. No. 3,282,955; however, they have not been commercially successfull probably because of inadequate sludge dispersant activity.

Reaction products of hydrocarbon substituted succinic anhydride, e.g., polyisobutenylsuccinic anhydride, with compounds containing both an amine group and a hydroxy group have been suggested or investigated in the prior art. For example, United Kingdom Specification No. 809,001 teaches corrosion inhibitors comprising a multiple salt complex derived from the reaction product of hydrocarbyl substituted dicarboxylic acids and hydroxy amines (including 2-amino-2-methyl-1,3-propanediol) [AMP] and tris-(hydroxymethyl)-amino methane [THAM]. Further, United Kingdom Specification No. 984,409 teaches ashless, amide/imide/ester type lubricant additives prepared by reacting an alkenylsuccinic anhydride, said alkenyl group having 30 to 700 carbon atoms, with a hydroxy amine including THAM. In contrast to the foregoing, German (DOS) No. 2,512,201 teaches that the reaction of a hydrocarbyl dicarboxylic acid material, i.e. acid or anhydride, or ester, with certain classes of amino alcohols, under certain conditions including metal salt promotion, will result in products containing one or two heterocyclic ring structures, namely, an oxazoline ring, and that products containing at least one oxazoline ring can be tailored for various functions, such as anti-rust agents, detergents, or dispersants for oleaginous compositions including lube oil, gasoline, turbine oils and oils for drilling applications. In none of the foregoing is there any suggestion that the reaction products could be usefully borated.

In contrast to the lubricating oil additive teachings of the prior art, mono-oxazolines have been usefully borated for gasoline additive applications to alleviate the adverse effects of combustion engine deposits, suppress surface ignition and carburetor icing (see U.S. Pat. Nos. 2,948,597; 2,965,459; 2,993,765; 3,030,374; 3,030,375; 3,070,603). Such gasoline additives are not suitable for lubricating oils since they lack satisfactory sludge dispersant activity and offer no teaching that they would be useful to inhibit the acid-induced catalytic decomposition of the lubricating oil.

Dicarboxylic acid lactone type products have also been provided with anti-rust and/or dispersant properties by reaction with hydroxy amines such as ethanolamine and diethanolamine (see U.S. Pat. Nos. 3,248,187 and 3,620,977).

SUMMARY OF THE INVENTION

It has now been found that a hydrolytically stable borated oxazoline lubricating oil additive which has unexpectedly enhanced varnish-inhibition activity can be realized by condensing a boron compound, e.g. boric acid, with the hydroxy alkyl groups of the oxazoline ring of an oil-soluble hydrocarbyl substituted oxazoline material when from about 0.1 to 2.0, preferably 0.3 to 1.0 wt. % of boron as a borate ester, is present in said material.

Although the boron can sometimes be introduced readily at temperatures of up to about 200° L C. by transesterification of said oxazoline material, undesirable viscosity increases and gel formation can occur. Moreover, introduction of the boron via an acidic compound, such as boric acid, at such high temperatures converts the oxazoline material by destruction of the oxazoline ring into undefined mixtures of boron containing imide/amide products of reduced sludge dispersant and/or varnish-inhibition activity.

It has been now further discovered that boric acid can be used with little if any destruction of the oxazoline ring when esterification is effected at a temperature of not greater than 120° C., preferably from about 60° to 100° C, thus preserving the enhanced dispersant activity resulting from the presence of the intact borated oxazoline structure.

Thus in accordance with this invention, there is provided a lubricating oil composition comprising a major amount of lubricating oil and a minor but dispersing amount of a dipersing and varnish inhibiting oil-soluble borated oxazoline material containing from about 0.1 to 2.0 wt. % boron and further characterized by from one to two oxazoline rings and substantially saturated hydrocarbon group containing at least about 50 carbon atoms.

The several types of preferred borated oxazoline materials can be illustrated by the following corresponding structural formulae:

(A) Borated hydrocarbyl substituted mono-oxazoline

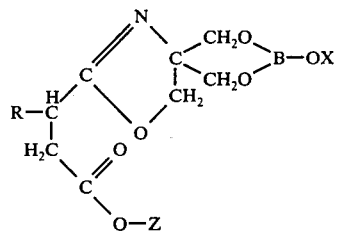

(B) Borated hydrocarbyl substituted bis-oxazoline

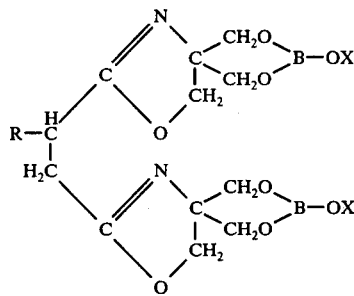

(C) Borated hydrocarbyl lactone oxazoline

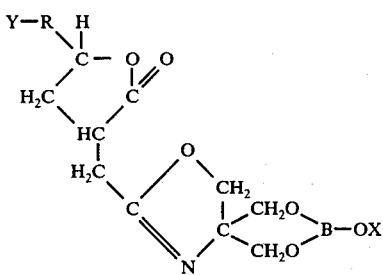

In all of the foregoing formulae, R refers to the oil-solubilizing hydrocarbyl substituent, preferably an alkenyl substituent, having a ($\overline{M}_n$) ranging from about 700 to 140,000 (alternatively having from about 50 to 10,000 carbons); preferably 900 to 20,000; and optimally, about 1200 to 5,000, X refers to hydrogen, a hydrocarbyl (preferably alkyl) or a heterocarbyl group containing from 4 to 20 carbons and when X is hydrogen the corresponding cyclic and acyclic boron anhydrides of said oxazolines are encompassed in said preferrd borated oxazoline materials, Y is selected from the group consisting of hydrogen, hydroxyl, sulfo, alkylthio (RS—), alkyldithio (RSS—), and a sulfur bridge, e.g., —S— and —S—S—, joining two lactone oxazoline units together and Z represents an apparent internal ester linkage with a hydroxy alkyl group of said oxazoline ring; T as defined later.

DETAILED DESCRIPTION OF THE INVENTION

The hydrocarbyl substituted dicarboxylic acid material, i.e., acid or anhydride, or ester which is used to produce the dispersants and/or varnish-inhibitors includes alpha-beta unsaturated $C_4$ to $C_{10}$ dicarboxylic acid, or anhydrides or esters thereof, such as fumaric acid, itaconic acid, maleic acid, maleic anhydride, chloromaleic acid, dimethyl fumarate, etc., which are substituted with a hydrocarbyl group, usefully a hydrocarbon chain containing at least 50 carbons (branched or unbranched) and includes long hydrocarbon chains, generally an olefin polymer chain.

In general, these hydrocarbyl substituted dicarboxylic acid materials and their preparation are well known in the art, for example see U.S. Pat. Nos. 3,219,666; 3,172,892; 3,272,746; the aforementioned prior art patents; as well as being commercially available, e.g., polyisobutylene succinic anhydride.

The dicarboxylic acid material can be illustrated by an alkenyl substituted anhydride which may contain a single alkenyl radical or a mixture of alkenyl radicals variously bonded to the cyclic succinic anhydride group, and is understood to comprise such structures as:

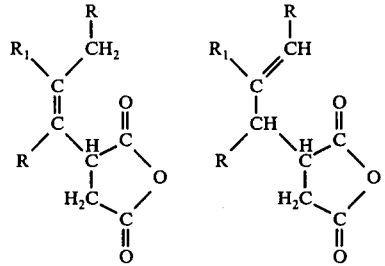

wherein R is hydrogen or lower hydrocarbyl and $R_1$ is hydrocarbyl or substituted hydrocarbyl having from 50 to about 10,000 and more carbons, and preferably from 60 to about 300 carbons. The anhydrides can be obtained by well-known methods, such as the Ene reaction between an olefin and maleic anhydride or halo-succinic anhydride or succinic ester (U.S. Pat. No. 2,568,876). In branched olefins, particularly branched polyolefins, R may be hydrogen or methyl and $R_1$ at least a $C_{50}$ long chain hydrocarbyl group. However, the exact structure may not always be ascertained and the various R and $R_1$ groups cannot always be precisely defined in the Ene products from polyolefins and maleic anhydride.

Suitable olefins include butene, isobutene, pentene, decene, dodecene, tetradecene, hexadecene, octadecene, eicosene, and polymers of propylene, butene, isobutene, pentene, decene and the like, and halogen-containing olefins. The olefins may also contain cycloalkyl and aromatic groups.

With 2-chloromaleic anhydride and related acylating agents, alkenylmaleic anhydride reactants are formed. Derivatization of these reactants also afford useful oxazoline products.

Preferred olefin polymers for reaction with the unsaturated dicarboxylic acids are polymers comprising a major molar amount of $C_2$ to $C_5$ monoolefin, e.g., ethylene, propylene, butylene, isobutylene and pentene. The polymers can be homopolymers such as polyisobutylene, as well as copolymers of two or more of such olefins such as copolymers of: ethylene and propylene; butylene and isobutylene; propylene and isobutylene; etc. Other copolymers include those in which a minor amount of the copolymer monomers, e.g., 1 to 20 mole % is a $C_4$ to $C_{18}$ non-conjugated diolefin, e.g, a coplymer of isobutylene and butadiene; or a copolymer of ethylene, propylene and 1,4-hexadiene; etc.

The olefin polymers will usually have $(\overline{M}_n)$s within the range of about 700 and about 140,000, more usually between about 900 and about 10,000. Particularly useful olefin polymers have $(\overline{M}_n)$s of about 1200 to 5000 with approximately one terminal double bond per polymer chain. An especially valuable starting material for a highly potent dispersant additive are polyalkenes e.g., polyisobutylene, having about 90 carbons.

OIL-SOLUBLE OXAZOLINE REACTION PRODUCT

Generally, useful oil-soluble oxazoline reaction products and their methods of preparation are fully described in German Patent Application DOS No. 2,512,201 which is fully incorporated herein by reference thereto. This oxazoline dispersant which forms a portion of the inventive combination can be characterized in its preferred form as an oil-soluble product obtained from heating together a molar equivalent of a hydrocarbon substituted $C_4$-$C_{10}$ mono-unsaturated dicarboxylic acid material having more than about 50 carbon atoms per dicarboxylic acyl group and from 1 to 2, preferably 1.5 to about 2, molar equivalents of a 2,2-disubstituted-2-amino-1-alkanol having 2 to 3 hydroxy groups and containing a total of 4 to 8 carbons at a temperature of from about 140° C. to 240° C. until cessation of water evolution indicating completion of the oxazoline reaction. This referenced amino-alkanol which readily produces the oxazoline rings requisite for this dispersant according to this invention can be represented by the formula

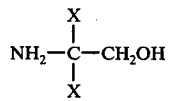

wherein X is an alkyl, or hydroxy alkyl group, with at least one of the X substituents being a hydroxy alkyl group of the structure $-(CH_2)_n OH$, wherein $n$ is 1 to 3:

Examples of such 2,2-disubstituted amino-alkanols, include 2-amino-2-methyl-1,3-propanediol, 2-amino-2-(hydroxymethyl)-1,3-propanediol (also known as tris(hydroxymethyl) aminomethane or THAM), 2-amino-2-ethyl-1,3-propanediol, etc. Because of its effectiveness, availability and cost, the THAM is particularly preferred. It is to be noted that other amino alcohols such as ethanolamine, propanolamine and butanolamine which lack the 2,2-disubstitution, do not afford the oxazoline product. The requisite $(\overline{M}_n)$ ranges of these products have already been specified.

The formation of the preferred oxazoline dispersants in high yield, can be effected by adding about 1.0 (to obtain the monooxazoline) to about 2 (to obtain the bisoxazoline) mole equivalent of the aforesaid 2,2-disubstituted-2-amino-1-alkanol per mole equivalent of the dicarboxylic acid material, with or without an inert diluent, and heating the mixture at 140°–240° C., preferably 160°–205° C., optimally 170°–190° C. for ½ to 24, more usually 2 to 8 hours, until the reaction is complete.

Completion of the oxazoline reaction can be readily ascertained by using periodic infrared spectral analysis for following oxazoline formation (oxazoline peak forms at 6.0 microns), or by the cessation of water evolution of about 1.5 to 3.0 moles of water.

Although not necessary, the presence of small amounts, such as 0.01 to 2 wt. %, preferably 0.1 to 1 wt. % based on the weight of the reactants, of a metal salt can be used in the reaction mixture as a catalyst. The metal catalyst can be later removed by filtration or by washing a hydrocarbon solution of the product with a lower alcohol, such as methanol, ethanol, isopropanol, etc., or an alcohol/water solution.

Alternatively, the metal salt can be left in the reaction mixture, as it appears to become stably dispersed, or dissolved, in the reaction product and depending on the metal, it can contribute performance benefits to the lubricating oil. This is believed to occur with the use of zinc catalysts in lubricants.

Inert solvents which may be used in the oxazoline reaction include hydrocarbon oils, e.g., mineral lubricating oil, kerosene, neutral mineral oils, xylene, halogenated hydrocarbons, e.g., carbon tetrachloride, dichlorobenzene, tetrahydrofuran, etc.

Metal salts that may be used as promoters or catalysts include carboxylic acid salts of Zn, Co, Mn, Ni and Fe. Metal catalysts derived from strong acids (HCl, sulfonic acids, $H_2SO_4$, HNO, etc.) and bases tend to diminish the yield of the oxazoline products and instead favor imide or ester formation. For this reason, these strong acid salts or basic salts are not preferred and usually will be avoided. The carboxylic acids used to prepare the desired promoters include $C_1$ to $C_{18}$, e.g., $C_1$ to $C_8$ acids, such as the saturated or unsaturated mono- and dicarboxylic aliphatic hydrocarbon acids, particularly fatty acids. Specific examples of such desired carboxylic acid salts include zinc acetate, zinc formate, zinc propionate, zinc stearate, manganese(ous) acetate, iron tartarate, cobalt(ous) acetate, nickel acetate etc. Zinc salts such as zinc acetate and zinc oxide, are preferred. Metal salts include the oxides.

It is preferred that the metal salt promoter be present at or near the onset of the reaction for greatest effect. The zinc salt promoter gradually dissolves by forming, inter alia, zinc complexes with the oxazoline product. Significantly and unexpectedly, the presence of zinc in the oxazoline product apparently contributes performance benefits to the lubricating oil.

While not known with complete certainty, it is believed that the reaction of the hydrocarbyl substituted dicarboxylic acid material, e.g., a substituted succinic anhydride with the amino alcohol of the invention, e.g., about 1.5 to 2 equivalents of 2,2-disubstituted-2-aminomethanol such as tris-hydroxymethylaminomethane (THAM), gives oxazoline, e.g. a mixture of monooxazoline and bis-oxazoline to all bis-oxazoline via the intermediacy of several discrete reaction species. If an acid anhydride is used, the initial transformation appears to involve the scission of the anhydride by the hydroxyl group of one mole of the amino alcohol to yield a hemi ester. Addition of another mole equivalent of amino alcohol is believed to form the amic acid amine salt, which then upon further heating, undergoes cyclodehydration to the final bis-oxazoline product.

The promoting effect of metal salts, such as zinc acetate ($ZnAc_2$), on oxazoline formation is very likely ascribable to the favorable polarization of the amide group by the zinc salt towards attack by the hydroxy function of the amino alcohol reactant. It is believed that the dissolved zinc salt ultimately coordinates with the oxazoline ring.

OIL-SOLUBLE LACTONE OXAZOLINE MATERIAL

This group of materials which feature vicinal lactone and oxazoline ring systems fully described in the co-pending U.S. patent application Ser. No. 726,206 filed Sept. 24, 1976 of common assignee which is fully incorporated herein by reference thereto. This group of materials can be represented by the formula:

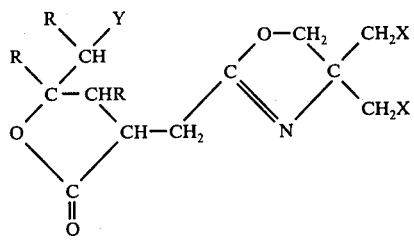

wherein R is selected from the group consisting of hydrogen and alkyl radicals containing from 1 to 400 or more carbons, X is selected from the group consisting of an alkyl or hydroxy alkyl group and at least one of the X substituents and preferably both of the X substituents being a hydroxy alkyl group of the structure —(CH$_2$)$_n$OH where $n$ is 1 to 3 and Y is selected from the group consisting of hydrogen, hydroxyl, sulfo, alkylthio (TS—), alkyldithio (TSS—), and a sulfur bridge, e.g., —S— and —S—S—, joining two lactone oxazoline units together as depicted below wherein $z$ is a number ranging from 1 to 4 and T is defined hereafter as containing 1 to 50, preferably 2 to 20 carbons.

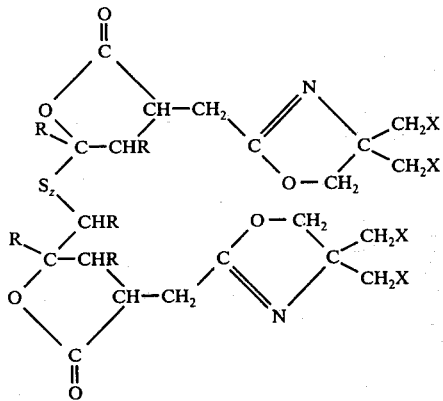

Preferred herein is polyisobutyl lactone oxazoline of number average molecular weight ranging from about 800 to 100,000 prepared by the reaction of equimolar proportions of polyisobutyl lactone carboxylic acid with tris-[hydroxymethyl] aminomethane at a temperature from about 100°–240° C., preferably 150°–180° C. until one mole of H$_2$O per mole of reactant is removed from the reaction.

These hydrocarbon soluble compounds have at least 50 carbons in the substantially saturated aliphatic hydrocarbyl group and a carboxylic acid group of the dicarboxylic acid material converted into a lactone ring and another carboxylic acid group converted into an oxazoline ring as a result of the reaction of at least equimolar amounts of said hydrocarbon substituted dicarboxylic acid lactone material and a 2,2-disubstituted-2-amino-1-alkanol having 1 to 3 hydroxy groups and containing a total of 4 to 8 carbons.

These precursor alkyl lactone oxazolines of the present invention can be prepared as noted by heating together alkyl lactone acids, esters or amides with a 2,2-disubstituted-2-amino-1-alcohol, such as tris-(hydroxylmethyl) aminomethane, as expressed in the following equation:

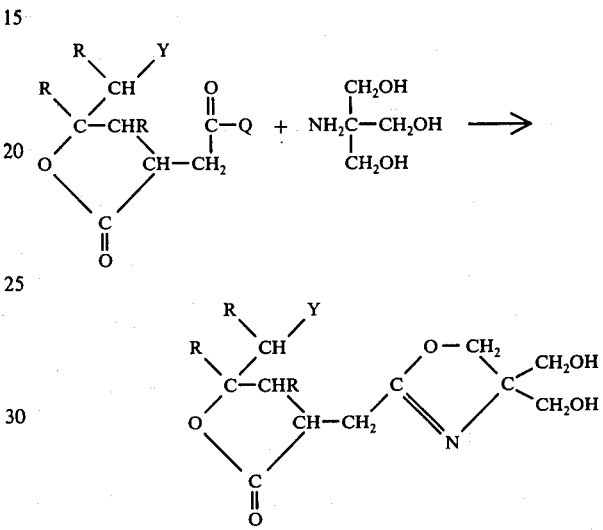

The preparation of said alkyl lactone reactants involves a lactonization of said hydrocarbyl substituted dicarboxylic acid material generally an alkenyl succinic acid analog obtained via the Ene reaction of an olefin with an alpha-beta unsaturated C$_4$ to C$_{10}$ dicarboxylic acid, or anhydrides or esters thereof, such as fumaric acid, itaconic acid, maleic acid, maleic anhydride, dimethyl fumarate, etc.

Unsubstituted or simple lactone reactants (Y=H) are readily obtained by the acid-catalyzed lactonization of an alkenyl dicarboxylic acid analog, the latter being derived from the ring scission of an alkenyl succinic anhydride with water, an alcohol or an amine as shown below wherein HQ represents water, alcohols containing from 1 to 10 carbons and dialkyl amines containing from 2 to 10 carbons and R is as previously defined.

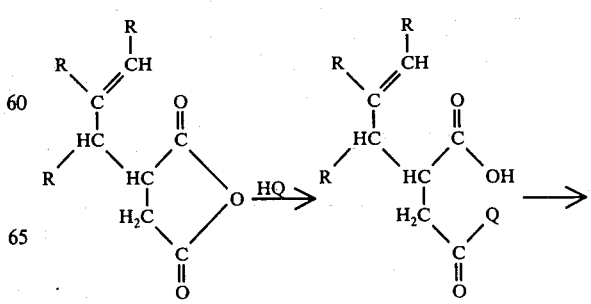

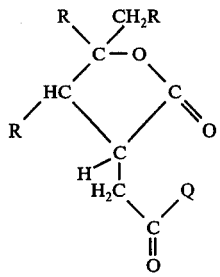

The reaction with HQ is assumed to open the anhydride at the least congested carbonyl group and form a succinic acid, hemi-ester or amic acid product which in the presence of an acid catalyst cyclizes mostly to the 5-ring lactone product as shown above.

It is possible to use alkenyl substituents with the double bond in the 1, 2, or 3-position or even double bonds further out on the hydrocarbyl chain since the acid catalyst is capable at moving it into a position suitable for lactone formation. In general, the size of the lactone ring formed will depend upon, inter alia, the position of the double bond, and which carboxylic acid group participates in the lactone forming reaction. As a consequence, both 5- and 6-ring (or larger ring) lactones can be envisaged as illustrated below:

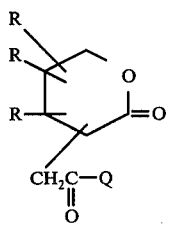

For convenience, the products of the present invention are usually shown as 5-ring lactones although larger ring lactone products can also be present.

Lactonization Catalysts

The intramolecular cyclization step involved in the process of this invention must be carried out in the presence of an acid-type catalyst in order to effect formation of the lactone. Suitable catalysts include the mineral acids such as hydrochloric acid, sulfuric acid, perchloric acid and phosphoric acid; the sulfonic acids such as the alkanesulfonic acids and the arylsulfonic acids; the Lewis type acids such as aluminum chloride, boron trifluoride, antimony trichloride, and titanium tetrachloride; low molecular weight sulfonic acid type ion exchange resin materials, such as cross-linked sulfonated polystyrene which is commercially available as Dowex-50. The alkanesulfonic acid catalysts are preferably the lower alkanesulfonic acids containing from 1 to 12 carbon atoms, for example, methanesulfonic acid, ethanesulfonic acid, propanesulfonic acid, and butanesulfonic acid. If desired, a mixture of lower alkane sulfonic acids can be used and such a mixture containing methane, ethane, and propanesulfonic acids is commercially available. Ordinarily, the alkanesulfonic acid will comprise from 92 to 95% sulfonic acid, from 1 to 2% sulfuric acid, and from 3 to 6% water. The arylsulfonic acid catalyst which can be used in the process includes the benzenesulfonic acids, toluenesulfonic acid, and chlorobenzenesulfonic acids, with p-toluenesulfonic acid and 4-chloro-benzenesulfonic acid being preferred.

The amount of catalyst present in the reaction zone can be varied over wide limits depending upon the nature of the reactants and the catalyst used. The amount of catalyst used is also determined to a considerable extent by the temperature selected for conducting the reaction. Thus, at higher temperatures the amount of catalyst required in the reaction is less than when lower temperatures are used and the use of excessive amounts of catalyst at the more elevated temperatures will promote the formation of undesired side products. Ordinarily, the amount of catalyst used will be between about 0.1 up to 10% by weight of the amount of the alkenyl succinic anhydride reactant.

Substituted Lactone Reactants

The presence of certain heteroatoms adjacent to the novel lactone oxazoline ring combination ofttimes endows the novel lactone oxazoline system with other desirable properties such as antioxidation and anticorrosion activity. In the present invention, we have devised novel ways of introducing hydroxyl, thiyl, sulfide, sulfoxide, sulfone and sulfo groups adjacent to the lactone oxazoline functions as described below:

Hydroxyl and Epoxy Lactone Reactants

Hydroxyl containing lactone reactants are prepared via the addition of peracids, hydrocarbyl peroxides or aqueous hydrogen peroxide to alkenyl succinic acid, hemi-ester or amide reagents as shown below:

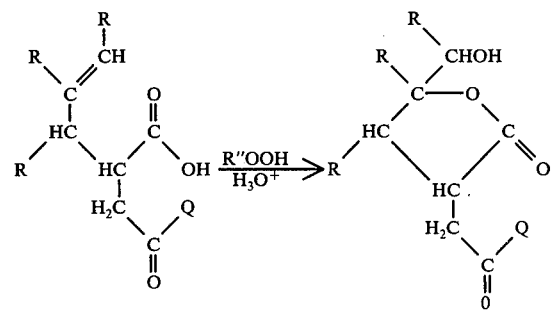

wherein Q is as previously defined and R″ represents hydrogen, acyl group containing from 2 to 20 carbons or alkyl group containing from 2 to 20 carbons. As an alternate, the epoxidation of alkenyl succinic anhydride, with peracids gives epoxy anhydrides which can react with (1) water, alcohols or amines to generate the desired hydroxy-substituted lactone reactants or (2) directly with THAM to give the lactone oxazoline endproducts.

The thiyl substituted lactones can be conveniently prepared via (1) thiol-induced scission of the epoxide ring in epoxy anhydrides as shown below wherein T represents alkyl, aryl or heterocyclic groups containing from 1 to 50 carbons

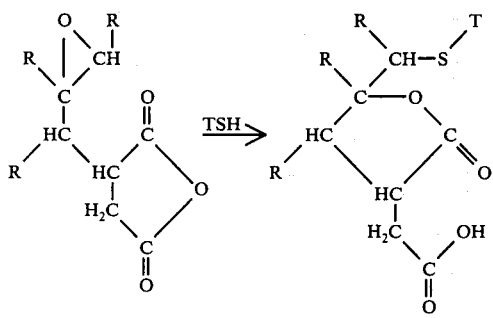

or via (2) sulfenyl halide addition to the double bond in alkenyl succinic acids or esters followed by lactonization via an internal displacement of halide as shown below:

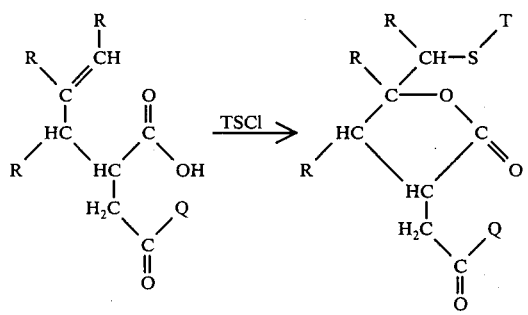

wherein T is defined as above.

The type of thinyl substituted lactone product will depend upon (i) the mode of epoxide cleavage by the thiol reagent and (ii) the mode of addition of the sulfenyl chloride to the double bond in the alkenyl succinic acid, ester or amide reactant.

With the sulfur halides ($S_xCl_2$, where $x$ is 1–4), thio, dithio and polythio bis-lactones are formed. Subsequent reaction of the latter with THAM affords the corresponding thio-bis-lactone oxazoline products.

Oxidation of the mono-thio-bis-lactones with peroxides can yield both sulfoxides and sulfones. In the case of the dithio-bis-lactones, oxidation affords sulfo-containing lactones.

In another approach thiyl lactones can also be designed by addition of the sulfenyl chloride reagent to the alkenyl succinic anhydride. Lactonization of the adduct can then be effected by either reacting (i) the sulfenyl chloride adduct per se, or (ii) the dehydrohalogenated adduct with an alcohol, water or an amine. Lactonization of the dehydrohalogenated thiyl substituted anhydride via option (ii) is preferably conducted in the presence of an acid catalyst.

Examples of useful thiols in preparing thiyl lactones via epoxide cleavage include alkyl and aryl thiols and heterocyclic thiols such as 2-mercapto-benzothiazole. Dithiophosphoric acids, e.g., $(RO)_2P(=S)$—SH, are also useful in designing phosphorus-containing products. In an alternate synthetic approach, the sulfenyl chloride analogs of the above-described thiols can be added to alkenyl succinic acid analogs to give the desired thiyl-substituted lactone reagents.

In another embodiment of the present invention, the reaction of chlorosulfonic acid or its equivalent, e.g., $SO_3$ and its complexes, with alkenylsuccinic anhydrides gives adducts which upon hydration yield sulfo lactone acids. Treatment of the latter with THAM can under suitable conditions generate sulfo lactone oxazoline end-products, reactants remains intact, and novel lactone oxazoline products are formed exclusively.

The formation of the lactone oxazoline materials in a very high yield, can be effected by adding at least about 1 molar equivalent of the aforesaid 2,2-disubstituted-2-amino-1-alkanol per mole equivalent of the polyalkyl lactone acid, ester or amide with or without an inert diluent, and heating the mixture at 100°–240° C., preferably 170°–220° C. until a reaction is complete by infrared analysis of the product showing maximal absorption for oxazoline.

Although not necessary, the presence of small amounts such as 0.01 to 2 wt. %, preferably 0.1 to 1 wt. %, based on the weight of the reactants, of a metal salt can be used in the reaction mixture as a catalyst. The metal catalyst can later be removed by filtration or by washing a hydrocarbon solution of the product with a lower alcohol, such as methanol, ethanol, isopropanol, etc., or an alcohol/water solution.

Alternatively, the metal salt can be left in the reaction mixture, as it appears to become stably dispersed, or dissolved, in the reaction product, and depending on the metal, it may even contribute performance benefits to the oil or gasoline. This is believed to occur with the use of zinc catalysts in lubricants.

Inert solvents which may be used in the above reaction include hydrocarbon oils, e.g., mineral lubricating oil, kerosene, neutral mineral oils, xylene, halogenated hydrocarbons, e.g., carbon tetrachloride, dichlorobenzene, tetrahydrofuran, etc.

Metal salts that may be used as catalysts in the invention include carboxylic acid salts of Zn, Co, Mn and Fe. Metal catalysts derived from strong acids (HCl, sulfonic, acid, $H_2SO_4$, $HNO_3$, etc.) and bases, tend to diminish the yield of the oxazoline products and instead favor imide or ester formation. For this reason, these strong acid catalysts or basic catalysts are not preferred and usually will be avoided. The carboxylic acids used to prepare the desired catalysts, include $C_1$ to $C_{18}$, e.g., $C_1$ to $C_8$ acids, such as the saturated or unsaturated mono- and dicarboxylic aliphatic hydrocarbon acids, particularly fatty acids. Specific examples of such desired carboxylic acid salts include zinc acetate, zinc formate, zinc propionate, zinc stearate, manganese(ous) acetate, iron tartrate, cobalt(ous) acetate, etc. Completion of the oxazoline reaction can be readily ascertained by using periodic infrared spectral analysis for following oxazoline formation (C=N absorption band at 6.0 microns) until maximized relative to lactone absorption or by the cessation of water evolution.

Oil-Soluble Borated Oxazoline Reaction Products

The boron compound useful in the reaction with the oil-soluble mono-and bis-oxazolines and the lactone oxazolines include boron oxide, boron oxide hydrate, boron acids such as boronic acid [e.g., alkyl-B(OH)$_2$ or aryl-B(OH)$_2$] and boric acids, preferably $H_3BO_3$, and esters of such boron acids.

Specific examples of boronic acids include methyl boronic acid, phenyl-boronic acid, cyclohexyl boronic acid, p-heptylphenyl boronic acid and dodecyl boronic acid.

The boric acid esters include mono-, di- and tri-substituted organic esters of boric acid with alcohols or phenols such as, e.g., butanol, octanol, cyclohexanol, cyclopentanol, ethylene glycol, 1,3-butanediol, 2,4-hexanediol, polyisobutene substituted phenols. Lower alcohols, 1,2-glycols, and 1,3-glycols, i.e., those having less than about 8 carbon atoms are especially useful for preparing the boric acid esters for the purpose of this invention. Methods for preparing the esters of boron acid are known and disclosed in the art (such as "Chemical Reviews" pages 959–1064, volume 56).

The general process of forming the oil-soluble borated oxazolines of the invention by reacting the oxazoline material with the boron containing compound is usually carried out by heating a mixture of the reactants at a temperature above about 60° C., preferably within the range from about 80° C. to about 200° C. However, when boric acid or oxide is employed, the process is carried out at a lower temperature (such as 60° C. to 100° C.) preferably at about 80° C. The use of a solvent such as benzene, toluene, naphtha, mineral oil, xylene, n-hexane, or the like is often desirable in the above process to facilitate the control of the reaction temperature and removal of water; mineral oil is preferred to facilitate the products use as a lubricating oil additive.

The oil-soluble oxazolines react readily with the boron compounds, e.g., boric acid at these mildly elevated temperatures to form the boron esters of the invention. When the substituted oxazoline in the reaction has two available hydroxyl groups, such as with the mono-oxazoline or the oxazoline may be reacted with the boron compound in a molar ratio of 1:1 or 1:2. If water of reaction is formed in the reaction as with the preferred boric acid, it is necessary to remove all or a part of it from the reaction mixture by separating it overhead, either by blowing with an inert gas such as nitrogen or by simple azeotropic distillation and to keep the temperature below 100° C. to prevent destruction of the oxazoline ring.

Useful oxazoline materials according to this invention retain the oxazoline absorption band at 6.0–6.1 microns to a level at least that of the carbonyl absorption bond at 5.9 microns apparently due to imide decomposition products. It is preferred that the absorption at 6.0–6.1 microns be 25% greater than that exhibited at 5.9 microns.

When transesterification is used to react the boron to the hydroxy groups, the reaction temperature and time must be controlled in such a manner as to prevent excessive gelation of the product.

Boration of the oxazoline materials should provide from about 0.1 to 2.0 wt. %, preferably 0.2 to 1.0 wt. %, boron based on the weight of said material.

Use of the Borated Oxazoline Additives in Lubricating Oil Compositions

The oil-soluble borated oxazoline reaction products of the invention can be usefully incorporated in a wide variety of lubricating oil compositions, such as automotive crankcase lubricating oils, automatic transmission fluids, etc., in concentrations generally within the range of about 0.01 to 20 weight percent, e.g., 0.1 to 10 weight percent, preferably 0.3 to 3.0 weight percent, of the total composition. The lubricants to which the lactone-oxazoline products can be added include not only hydrocarbon oils derived from petroleum but also include synthetic lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; mixtures of mineral lubricating oil and synthetic oils in any proportion, etc.

When the products of this invention are used as multifunctional additives having detergents, anti-rust properties in petroleum fuels such as gasoline, kerosene, diesel fuels, No. 2 fuel oil and other middle distillates, a concentration of the additive in the fuel in the range of 0.001 to 0.5 weight percent, based on the weight of the total composition, will usually be employed.

The additive may be conveniently dispensed as a concentrate comprising a minor proportion of the additive, e.g., 20 to 90 parts by weight, dissolved in a major proportion of a mineral lubricating oil, e.g., 10 to 80 parts by weight, with or without other additives being present.

In the above compositions or concentrates, other conventional additives may also be present including dyes, pour point depressants, antiwear agents such as tricresyl phosphate or zinc dialkyldithiophosphates of 3 to 8 carbon atoms in each alkyl group, antioxidants, such as N-phenyl α-naphthaylamine, tert-octylphenol sulfide, 4,4′-methylene bis(2,6-di-tert-butyl phenol), viscosity index improvers such as ethylene-propylene copolymers, polymethacrylates, polyisobutylene, alkyl fumarate-vinyl acetate copolymers and the like, deemulsifiers such as polysiloxanes, ethoxylated polymers and the like.

This invention will be further understood by reference to the following examples, which include preferred embodiments of the invention.

EXAMPLE 1

Borated Bis-Oxazoline of Polyisobutenyl Succinic Anhydride

The polyisobutenyl succinic anhydride bis-oxazoline was obtained from the reaction of one mole of polyisobutenyl ($\overline{M}_n$ of 980) succinic anhydride having a Sap. No. of 80 with two moles of tris(hydroxy methylamino) methane according to the teachings of German DOS No. 2,512,201.

A solution of 900 gms. of the polyisobutenyl succinic anhydride-bis-oxazoline in 900 gms. of Solvent 150N mineral oil was charged into a 5 liter, 4-necked reaction flask. The solution was purged overnight at 80° C. with nitrogen and 148 gms. of tributyl borate (4.7 wt.% boron) were added. The mixture was refluxed at temperatures ranging from 130° C. to 160° C. for 1 hour after which the temperature was held at about 200° C. for 5 hours. The reaction mixture was thereafter sparged with nitrogen for an hour at about 200° C. The product was a dark viscous oily solution containing about 50 wt.% active ingredient and analyzed for 0.32 wt.% boron and 0.92 wt.% nitrogen. The infra-red absorption curve indicated no significant loss of the oxazoline structure (substantial absorption at 6 microns).

EXAMPLE 2

Borated Mono Oxazoline of Polyisobutylene Succinic Anhydride (2A) Two hundred grams (ca. 0.1 mole) of a 51–53% solution of polyisobutenyl succinic anhydride (PIBSA of ($\overline{M}_n$) of 960 and having a Saponification Number of 84) in Solvent 150 Neutral oil were mixed with 0.1 mole (12.1 g) of tris-(hydroxymethyl) aminomethane (THAM) and 0.1 g of zinc acetate. The mixture was then heated to 200° C. for 8–10 hours until all the water distilled off and the infrared spectrum showed prominent ester carbonyl and oxazoline (C=N) absorption bands at 5.75 and 6.03 microns as expected for the monooxazoline product. After the stripping period, the product was filtered hot through a filter cake of Celite 505. The filtrate analyzed for 0.69 wt.% nitrogen (Kjeldahl).

(2B) One hundred sixty-five grams (0.05 moles) of a 50% oil solution prepared as described above were mixed with 0.05 mole (33 g) of boric acid and gradually heated to 100° C. The infrared spectrum after ½ hour at 80° C. showed the disappearance of the characteristic absorption bands (3.0 and 9.6 micron) ascribable to the oxazoline reactant. The reaction product was then sparged with nitrogen at 100° C. for 1 hour to remove the water of reaction. The infrared spectrum of the final product showed a strong oxazoline absorption band at 6.03 microns which greatly exceeds the absorption at 5.87 microns (ascribed to carbonyl absorption from imide products). The 50 wt.% oil solution of the borated monooxazoline prepared above analyzed for 0.69 wt.% nitrogen (Kjeldahl) and 0.4 wt.% boron.

EXAMPLE 3

Borated Bis-Oxazoline of Polyisobutenyl ($M_n$ of 1300) Succinic Anhydride (3A) Five hundred grams (0.459 moles) of a (PIBSA) containing about 90 carbon atoms and having a Saponification Number of 103 were diluted with 557 g of Solvent 150 Neutral. The mixture was heated under a nitrogen blanket to 177° C. with stirring and 265 g (0.87 moles) of a 40% aqueous (THAM) solution and 3.4 g of zinc acetate (in solution) were added dropwise over a period of 2 hours. A reaction temperature of 177° C. with sparging was maintained during the addition to facilitate removal of the water vapor. Once the addition was completed, the reaction mixture was nitrogen stripped at 177° C. for 10 hours and thereafter filtered.

(3B) Three thousand grams of the filtrate (ca. 1.0 mole of the bis-oxazoline) prepared as above were mixed with 53.5 g of boric acid and heated gradually to 100° C. When the temperature reached 100° C., infrared analysis of the reaction mixture revealed that the absorption bands at 3.0 and 9.6 microns had completely disappeared indicating boration was completed. The reaction mixture was sparged with nitrogen at 100° C-100° C. for 1 hour to eliminate any water present, and then filtered.

The filtrate containing the borated bis-oxazoline product featured infrared absorption bands in the 5.8 to 6.1 micron region substantially unchanged from that observed for the bis-oxazoline product of 3(A) indicating retention of the oxazoline structure in the borated derivative. The absorption at 6.03 microns significantly exceeded the absorption at 5.87 microns. The filtrate analyzed for 1.13 wt.% nitrogen and 0.29 wt.% boron.

EXAMPLE 4

Borated Bis-Oxazoline of Polyisobutenyl ($M_n$ 960) Succinic Anhydride (A) Two hundred grams (ca. 0.1 mole) of a 51 wt.% solution of polyisobutenyl succinic anhydride [(PIBSA) of ($\overline{M}_n$) ≈ 960 and having a Saponification Number (SAP) of 84] in Solvent 150 Neutral were heated to about 100°-120° C. Then, 0.2 mole (24.2 g) of tris-(hydroxymethyl)aminomethane (THAM) and 0.1 g of zinc acetate were added. The mixture was heated to 180°-185° C. until the evolution of water subsided (after approximately 2 hours). The oxazoline (C=N) infrared absorption band of the product was maximal at that time. The product was filtered.

(B) 200 grams of the product filtrate from 4(A) (0.1 mole of bis-oxazoline) were mixed with 6.2 grams (0.1 mole) of boric acid and heated to 100° C. and maintained at that temperature for 1 hour. Infrared analysis showed the disappearance of the characteristic absorption bands at 3.0 and 9.6 microns indicating borate ester formation was complete. The reaction mixture was then sparged with nitrogen. The filtrate containing the borated bis-oxazoline product featured infrared absorption bands in the 5.8 to 6.1 micron region substantially unchanged from that observed for the bis-oxazoline product of 4(A) indicating retention of the oxazoline structure in the borated derivative of Ex. (4B). The absorption at 6.03 microns significantly exceeded the absorption at 5.87 microns. The filtrate analyzed for 1.2 wt.% nitrogen and 0.478 wt.% boron.

EXAMPLE 5

Reaction Product of Polybutenyl Succinic Anhydride, Tris(Hydroxymethyl) Aminomethane and Boric Acid This Example is a reproduction of Example 3 of U.S. patent application Ser. No. 494,789, filed Aug. 5, 1974 which is the priority application claimed for German DOS No. 2,534,922.

A mixture of 100 grams (0.05 mol.) of polybutenylsuccinic anhydride, prepared from a polybutene having about 130 carbon atoms and maleic anhydride reactant in the presence of t-butyl peroxide, and 6.05 grams (0.05 mol.) of tris(hydroxyl methyl) amino methane was added to a suitable reactor. The mixture was heated with stirring to about 175° C. and maintained at that temperature until no further water was taken off. The mixture was cooled to 75° C. and 3.5 grams (0.057 mols.) of boric acid was added along with 15 grams (0.2 mols.) of butanol. The reaction mixture was then refluxed to about 225° C. over a 10 hour period. The reaction product was filtered and topped to 165° C. at reduced pressure to produce a viscous liquid final product which was diluted to about 52 wt.% active ingredient with Solvent 150N mineral oil. Analysis on the diluted solution gave 0.237 wt.% boron and 0.31 wt.% nitrogen (Kjeldahl). Infrared analysis showed an intense absorption band at 5.87 microns (ascribable to imide products). By sharp contrast, the oxazoline absorption band at 6.03 microns had essentially disappeared.

EXAMPLE 6

Borated Polyisobutyl Lactone Oxazoline (A) Six hundred grams of a solution of Solvent 150 Neutral oil containing 51 wt.% of polybutenyl succinic anhydride (PIBSA of ($\overline{M}_n$) ≈ 960 and having a Saponification Number of 84) were mixed with 6 grams of water and 20 grams of Amberlyst 15 catalyst. The resulting mixture was heated at 100° C. for about 8-10 hours and then to 130° C. for 2 hours. Infrared analysis showed the presence of strong absorption bands at about 6.5-8.5 microns, characteristic of lactone acids. The product was diluted with hexane, filtered, and rotoevaporated at 80°-100° for 4 hours. The residue upon treatment with an excess of diethylamine featured an infrared spectrum with a strong lactone carbonyl absorption band at 5.64 microns.

(B) Two hundred grams (ca 0.1 mole of polyisobutyl lactone acid) of the product solution described above in Example 6A and 12.1 g (0.1 mole) of (THAM) were mixed into a reaction flask and gradually heated to about 180°-185° C. for 1-1½ hours. The product was diluted in 200 ml of hexane, filtered and rotoevaporated at 90° C. for 2 hours. Infrared analysis of the product solution containing about 50 wt. % polyisobutyl lactone oxazoline showed strong absorption bands at 5.65 and 6.0 microns ascribable to lactone oxazoline functionality. This product solution analyzed for 0.69 wt. % nitrogen (Kjeldahl) (theoretical N≈0.67%).

(C) 200 grams of the polyisobutyl lactone oxazoline solution (0.1 mole of lactone oxazoline) described above in Example 6(B) were heated to 120° C. and 0.1 mole (6.2g) of boric acid added portionwise for a period of 15 minutes. The mixture was sparged with nitrogen while heating to 150° C. for 1 hour to remove the water of formation. Infrared analysis of the product solution showed the disappearance of the absorption bands at 3.0 and 9.6 microns which are characteristic of the oxazoline reactants. The spectrum also showed the lactone carbonyl and oxazoline (C=N) absorption bands at 5.7 and 6.03 microns. This product solution (containing about 50 wt. % borated product) analyzed for 0.69 wt. % nitrogen (Kjeldahl) and 0.49 wt. % boron.

EXAMPLE 7

Borated Bis-Oxazoline of Polyisobutenyl ($M_n$ of 1300) Succinic Anhydride

This example utilizes tributylborate as the boron compound as did Example 1 although in this instance the product realized was highly viscous.

A polyisobutenyl bisoxazoline prepared from polyisobutenyl succinic anhydride of about 90 carbon atoms and with a Saponification Number of 103 was adjusted with solvent oil to a nitrogen value of one weight percent. 350 grams of this material were nitrogen sparged at 125° C. for one hour to remove traces of water and light ends. Thirty grams (0.13 moles) of tributyl borate were added and the reaction flask fitted with a cold finger condenser for the collection of the overhead. The temperature pattern was 160° C. for 1 hour, 170° C. for a second hour, 180° C. for 3½ hours then a nitrogen sparge at 200° C. for 1½ hours. The collected overhead was 27 grams of mostly butanol. The product contained 1.03 wt. % nitrogen and 0.399 wt. % boron. It was a dark brown gel-like material with a Saybolt Universal viscosity at 210° F. of 5643 seconds, an increase of over 400%. The starting bis-oxazoline had a viscosity at 210° F. of 1371 seconds.

EXAMPLE 8

High Temperature Boration of Bis-Oxazolines of Polyisobutenyl Succinic Anhydride These following examples where boration with boric acid is conducted at about 200° C. (225° C. is that condition of Example 3 of DOS No. 2,534,922 which is the boration temperature of Example 5) indicate that a substantial amount of the oxazoline in the PIBSA-Bis-oxazoline is converted into imide type products as determined by infrared analysis.

(A) One hundred sixty-five grams of an oil solution of polybutenyl ($M_n$ of 960) bisoxazoline (0.05 moles, 50 wt. % a.i.) were mixed with 0.05 mole (3.3 g) of boric acid and heated to 200° C. for 8 hours. When the temperature reached 200° C., the infrared spectrum showed the absence of the 9.6 micron absorption band but the intensity of the oxazoline band became weaker and the imide absorption band at 5.9 microns increased in size. At the end of the 8-hour heating period, the infrared spectrum of the product showed a intense imide absorption band at 5.9 microns and virtually no oxazoline absorption in the 6.0-6.1 microns region. The product solution (50 wt. % a.i.) analyzed at 1.06 wt. % N (Kjeldahl) and 0.37 wt. % boron.

(B) Three hundred grams of (0.1 mole, 50% a.i.) polyisobutenyl bis-oxazoline prepared as described in Example 3(A) were mixed with 6.4 g of boric acid and heated to 200° C. for 7 to 8 hours. Infrared analysis at this juncture showed a substantial reduction in the intensity of the oxazoline band at 6.03 microns. By the end of the heating period (10 hours), IR analysis revealed that the oxazoline band had completely disappeared; and the resulting product upon cooling, afforded a gel-like material. Analysis of this product gel (~50 wt. % a.i.) showed 1.13 wt. % N (Kjeldahl) and 0.44 wt. % boron.

EXAMPLE 9

Sludge Inhibition Bench (SIB) Test

The products of Examples 2, 3, 4 and 5 were subjected to a Sludge Inhibition Bench (SIB) Test which has been found after a large number of evaluations, to be an excellent test for assessing the dispersing power of lubricating oil dispersant additives.

The medium chosen for the Sludge Inhibition Bench Test was a used crankcase mineral lubricating oil composition having an original viscosity of about 325 SUS at 100° F. that had been used in a taxicab that was driven generally for short trips only, thereby causing a buildup of a high concentration of sludge precursors. The oil that was used contained only a refined base mineral lubricating oil, a viscosity index improver, a pour point depressant and zinc dialkyldithiophosphate antiwear additive. The oil contained no sludge dispersants. A quantity of such used oil was acquired by draining and refilling the taxicab crankcase at 1000-2000 mile intervals.

The Sludge Inhibition Bench Test is conducted in the following manner. The aforesaid used crankcase oil, which is milky brown in color, is freed of sludge by centifuging for ½ hour at about 39,000 gravities (gs.). The resulting clear bright red supernatant oil is then decanted from the insoluble sludge particles thereby separated out. However, the supernatant oil still contains oil-soluble sludge precursors which on heating under the conditions employed by this test will tend to form additional oil-insoluble deposits of sludge. The sludge inhibiting properties of the additives being tested are determined by adding to portions of the supernatant used oil, a small amount, such as 0.5 wt. %, on an active ingredient basis, of the particular additive being tested. Ten grams of each blend being tested is placed in a stainless steel centrifuge tube and is heated at 280° F. for 16 hours in the presence of air. Following the heating, the tube containing the oil being tested is cooled and then centrifuged for 30 minutes at about 39,000 gs. Any deposits of new sludge that form in this step are separated from the oil by decanting the supernatant oil and then carefully washing the sludge deposits with 15 ml. of pentane to remove all remaining oil from the sludge. Then the weight of the new solid sludge that has been formed in the test, in milligrams, is determined by drying the residue and weighing it. The results are reported as milligrams of sludge per 10 grams of oil, thus measuring differences as small as 1 part per 10,000. The less new sludge formed the more effective is the additive as a sludge dispersant. In other words, if the additive is effective, it will hold at least a portion of the new sludge that forms on heating and oxidation, stably suspended in the oil so it does not precipitate down during the centriging.

Using the above-described test, the dispersant action of the borated oxazolines of the present invention were compared with the corresponding non-borated oxazolines, the borated imidized product of German DOS No. 2,534,922 and a commercial dispersant referred to as PIBSA-TEPA. The PIBSA-TEPA was prepared by reaction of 1 mole of tetraethylene pentamine with 1.5 moles of polyisobutenyl succinic anhydride (Sap. No. 80) obtained from polyisobutylene of about 1000 number average molecular weight. The PIBSA/TEPA dispersant was used in the form of an additive concentrate containing about 50 weight percent PIBSA/TEPA in 50 wt. % mineral lubricating oil. This PIBSA/TEPA additive concentrate analyzed about 1.8% nitrogen, indicating that the active ingredient, i.e., PIBSA/TEPA per se, contained about 3.6% nitrogen. The test results are given in the table below.

TABLE I
SLUDGE DISPERSANCY TEST RESULTS

| Additive of Example | Mg Sludge/10 g. Oil at | |
|---|---|---|
| | %N | 0.5 wt.% |
| 2A | 0.69 | 2.58 |
| 2B | 0.69 | 4.36 |
| 3A | 1.13 | 0.94 |
| 3B | 1.13 | 3.69 |
| 4A | 1.2 | 5.6 |
| 4B | 1.2 | 2.93 |
| 5 | 0.31 | 8.84 |
| Blank | — | 10.0 |
| PIBSA/TEPA | 0.60 | 7.78 |

EXAMPLE 10

Evaluation of Products In Varnish Inhibition Test

Each test sample consisted of 10 grams of lubricating oil containing 0.07 of a gram of the additive concentrate (50% active) which results in a total of 0.35 wt. % additive present in the test sample. The test oil to which the additive is admixed was 9.93 grams of a commercial lubricating oil obtained from a taxi after 2,000 miles of driving with said lubricating oil. Each ten gram sample was heat soaked overnight at about 140° C. and thereafter centrifuged to remove the sludge. The supernatant fluid of each sample was subjected to heat cycling from about 150° C. to room temperature over a period of 3.5 hours at a frequency of about 2 cycles per minute. During the heating phase, the gas containing a mixture of about 0.7 volume percent $SO_2$, 1.4 volume percent NO and balance air was bubbled through the test samples and during the cooling phase water vapor was bubbled through the test samples. At the end of the test period, which testing cycle can be repeated as necessary to determine the inhibiting effect of any additive, the wall surfaces of the test flasks in which the samples were contained are visually evaluated as to the varnish inhibition. The amount of varnish imposed on the walls is rated to values of from 1 to 7 with the higher number being the greater amount of varnish. It has been found that this test correlates with the varnish results obtained as a consequence of carrying out an MS-VC engine test. The results which are recorded in Table II indicate that the borated oxazoline reaction products of the invention had superior varnish-inhibition activity to the non-borated counterparts and to the product of German DOS No. 2,534,922.

TABLE II

| 0.35 WEIGHT PERCENT OF ADDITIVE ADDED TO TEST OIL | | | |
|---|---|---|---|
| Test Sample | Borated | Additive of Example | VIB Rating |
| 1 | no | 2A | 6 |
| 2 | yes | 2B | 5 |
| 3 | no | 3A | 5 |
| 4 | yes | 3B | 4 |
| 5 | no | 4A | 5 |
| 6 | yes | 4B | 4 |
| 7 | yes | 5 | 7 |
| 8 | no | Blank | 11 |
| 9 | no | PIBSA/TEPA | 7 |

The data of Table II illustrate the outstanding varnish-inhibition activity of the borated additive products of the invention particularly when compared with a known commercial dispersant referred to as PIBSA-TEPA and to a borated dispersant reported in German DOS No. 2,534,922.

The numerous examples cited above illustrate the novel additives of the invention; the new processes devised in preparing these additives and the examples further illustrate the surprising dispersant and/or varnish inhibition activity when incorporated into lubricating oils.

The invention in its broader aspects is not limited to the specific details shown and described and departures may be made from such details without departing from the principles of the invention and with sacrificing its chief advantages.

What is claimed is:

1. A lubricating oil composition comprising a major amount of lubricating oil and a minor but dispersing amount of a sludge dispersing and varnish inhibiting oil-soluble borated oxazoline material containing from about 0.1 to 2.0 wt. % boron, wherein
said oxazoline material is formed by the reaction of
(A) a hydrocarbyl substituted $C_4$ to $C_{10}$ dicarboxylic acid or anhydride, wherein said hydrocarbyl group is a polymer of $C_2$ to $C_5$ monoolefin, said polymer having a molecular weight of about 900 and 10,000; and (B) a 2,2-disubstituted-2-amino-1-alkanol having 2 to 3 hydroxy groups and containing a total of 4 to 8 carbons and represented by the formula:

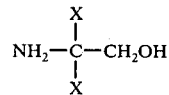

wherein X is an alkyl, or hydroxy alkyl group, with at least one of the X substituents being a hydroxy alkyl group of the structure $-(CH_2)_nOH$, said oxazoline material having one to two oxazoline rings.

2. The lubricating oil composition according to claim 1 wherein said borated oxazoline material is obtained from the reaction of one molar proportion of an alkenyl succinic anhydride or acid and from about 1.5 to about 2 molar proportions of said 2,2-disubstituted-2-amino-1-alkanol followed by condensation with a boron reactant selected from the group consisting of boron oxide hydrates, boron oxides, boron acids and esters of boron acids.

3. A composition comprising a major amount of an oil of lubricating viscosity and a minor but dispersing amount of an oil-soluble, borated derivative of the oxazoline reaction product of a substantially saturated aliphatic hydrocarbyl, substituted $C_4$-$C_{10}$ mono-unsaturated dicarboxylic acid material, said hydrocarbyl group having a number average molecular weight ranging from about 700 to about 140,000 with from at least 1 to about 2 mole equivalent, per mole equivalent of said dicarboxylic acid material, of a 2,2-disubstituted-2-amino-1-alkanol having 2 to 3 hydroxy groups and containing a total of 4 to 8 carbons, and which is represented by the formula:

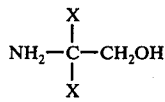

wherein X is an alkyl or hydroxyl alkyl group, with at least one of the X substituents being a hydroxyl alkyl group of the structure —$(CH_2)_n$OH wherein $n$ is 1 to 3, said reaction conditions being at a temperature of from about 140° C. to 240° C. for from ½ to 24 hours whereby at least one carboxylic acyl group is converted into an oxazoline ring, said reaction product being borated by condensation with a boron compound selected from the class consisting of boron oxide, boron acids and esters of boron acids in an amount to provide from about 0.1 to 2.0 wt. % boron based on the total weight of said borated ester derivative.

4. A composition according to claim 3, wherein said borated oxazoline reaction product is the mono-oxazoline product of an alkenyl succinic anhydride or acid which has been reacted with about one mole equivalent of tris-hydroxymethylaminomethane, said alkenyl substituent having a number average molecular weight within the range of about 1000 and about 20,000.

5. A composition according to claim 3 wherein said borated oxazoline reaction product is the bis-oxazoline product of hydrocarbon substituted succinic anhydride reacted with about two mole equivalent of tris-hydroxymethylaminomethane, said bis-oxazoline being condensed with boric acid at a temperature ranging from about 80° to 120° C.

6. A composition according to claim 1 wherein said borated oxazoline reaction product is the mono-oxazoline product of hydrocarbon substituted succinic anhydride which has been reacted with about one mole equivalent of tris-hydroxymethylaminomethane, said mono-oxazoline being further reacted with an amine which is an alkylene polyamine containing 2 to 12 nitrogen atoms, and wherein pairs of nitrogen atoms are joined by alkylene groups of 2 to 4 carbon atoms and subsequently condensed with boric acid at a temperature ranging from about 80° C. to 100° C.

7. A lubricant composition comprising a major proportion of a lubricant oil and from about 0.01 to 20% by weight of the oil-soluble borated oxazoline reaction product, of one mole equivalent alkenyl succinic acid or anhydride wherein said alkenyl substituent contains a chain of at least 50 carbons, with from at least 1 to about 2 mole equivalent tris-hydroxymethylaminomethane, further condensed by reaction with from 1 to 3 moles of a boron reactant selected from the group consisting of boron oxides, boron oxide hydrates, boron acids and esters of boron acids.

8. A composition according to claim 7 wherein said oil-soluble derivative is the reaction product of 1 to 2 moles of boric acid with a molar proportion of a bis-oxazoline product resulting from the reaction of said alkenyl succinic anhydride with about two mole equivalent of said tris-hydroxymethylaminomethane.

9. A lubricating oil composition comprising: a major amount of lubricating oil and 0.01 to 20 wt. % of an oil-soluble, borated lactone oxazoline reaction product obtained from heating together a molar proportion of a hydrocarbon substituted lactone acid material and one molar proportion of a 2,2-disubstituted-2-amino-1-alkanol having 1 to 3 hydroxy groups and containing a total of 4 to 8 carbons at a temperature of from 100°–240° C. until cessation of water evolution indicating completion of the oxazoline reaction and thereafter condensing said product with a boron compound selected from the class consisting of boron oxides, boron oxide hydrates, boron acids and esters of boron acids in an amount to provide from about 0.1 to 2.0 wt. % boron based on the total weight of said borated reaction product, wherein said lactone acid material is formed by converting one of the carboxy groups of a hydrocarbyl substituted $C_4$ to $C_{10}$ dicarboxylic acid or anhydride to a lactone, said hydrocarbyl substituent being a polymer of a $C_2$ to $C_5$ monoolefin, said polymer having a molecular weight of about 900 to 10,000.

10. A composition according to claim 9 wherein said amino-1-alkanol is tris-(hydroxymethyl) aminomethane and said boron compound is boric acid condensed at a temperature of from about 80° C. to 120° C.

11. A composition according to claim 1 wherein said borated oxazoline material has an infrared absorption at 6.03 microns which is greater than that at 5.87 microns.

12. An oil-soluble borated oxazoline material containing from about 0.1 to 2.0 wt. % boron, wherein
said oxazoline material is formed by the reaction of
(A) a hydrocarbyl substituted $C_4$ to $C_{10}$ dicarboxylic acid or anhydride, wherein said hydrocarbyl group is a polymer of $C_2$ to $C_5$ monoolefin, said polymer having a molecular weight of about 900 and 10,000; and (B) a 2,2-disubstituted-2-amino-1-alkanol having 2 to 3 hydroxy groups and containing a total of 4 to 8 carbons and represented by the formula:

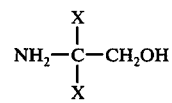

wherein X is an alkyl, or hydroxy alkyl group, with at least one of the X substituents being a hydroxy alkyl group of the structure —$(CH_2)_n$OH, said oxazoline material having one to two oxazoline rings.

13. The oxazoline material according to claim 12 wherein said oxazoline material is obtained from the reaction of one molar proportion of an alkenyl succinic anhydride or acid and from about 1.5 to about 2 molar proportions of said 2,2-disubstituted-2-amino-1-alkanol, followed by condensation with a a boron reactant selected from the group consisting of boron oxides, boron oxide hydrates, boron acids and esters of boron acids.

14. A borated oxazoline material which is a borated derivative of the oxazoline reaction product of a substantially saturated aliphatic hydrocarbyl, substituted $C_4$-$C_{10}$ mono-unsaturated dicarboxylic acid material, said hydrocarbyl group having a number average molecular weight ranging from about 700 to about 140,000 with from at least 1 to about 2 mole equivalent, per mole equivalent of said dicarboxylic acid material, of a 2,2- disubstituted-2-amino-1-alkanol having 2 to 3 hydroxy groups and containing a total of 4 to 8 carbons, and which is represented by the formula:

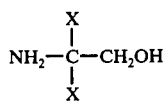

wherein X is an alkyl or hydroxyl alkyl group, with at least one of the X substituents being a hydroxyl alkyl group of the structure —$(CH_2)_nOH$ wherein $n$ is 1 to 3, said reaction conditions being at a temperature of from about 140° C. to 240° C. for from ½ to 24 hours whereby at least one carboxylic acyl group is converted into an oxazoline ring, said oxazoline reaction product being borated by condensation with a boron compound selected from the class consisting of boron oxides, boron oxide hydrates, boron acids and esters of boron acids in an amount to provide from about 0.1 to 2.0 wt. % boron based on the total weight of said borated ester derivative.

15. The oxazoline material of claim 14 wherein said material is the bis-oxazoline product of hydrocarbon substituted succinic anhydride reacted with about two mole-equivalent of tris-hydroxymethyl-aminomethane, said bis-oxazoline being condensed with boric acid at a temperature ranging from about 80° to 120° C. and having infrared absorption at 6.03 microns which significantly exceeds the infrared absorption at 5.87 microns.

16. The oxazoline material of claim 12 wherein said material is obtained from heating together a molar proportion of a hydrocarbon substituted lactone acid material and one molar proportion of a 2,2-disubstituted-2-amino-1-alkanol having 1 to 3 hydroxy groups and containing a total of 4 to 8 carbons at a temperature of from 100°-240° C. until cessation of water evolution indicating completion of the oxazoline reaction and thereafter condensing said product with a boron compound selected from the class consisting of boron oxides, boron oxide hydrates, boron acids and esters of boron acids in an amount to provide from about 0.1 to 2.0 wt. % boron based on the total weight of said borated reaction product, wherein said lactone acid material is formed by converting one of the carboxy groups of a hydrocarbyl substituted $C_4$ to $C_{10}$ dicarboxylic acid or anhydride to a lactone, said hydrocarbyl substituent being a polymer of a $C_2$ to $C_5$ monoolefin, said polymer having a molecular weight of about 900 to 10,000.

17. A process of making an oil-soluble borated oxazoline material according to claim 12 comprising the step of condensing said oxazoline material with said boron compound at a temperature of above about 60° C. for at least a time sufficient that the reaction product does not show infrared absorption at 3.0 and 9.6 microns with the restriction that when boric acid or oxide is employed, the temperature employed is from 60° C. to 100° C.

* * * * *

UNITED STATES PATENT OFFICE
CERTIFICATE OF CORRECTION

Patent No. 4,116,876  Dated September 26, 1978

Inventor(s) Stanley J. Brois et al

It is certified that error appears in the above-identified patent and that said Letters Patent are hereby corrected as shown below:

Column 9, line 27 after "below" insert

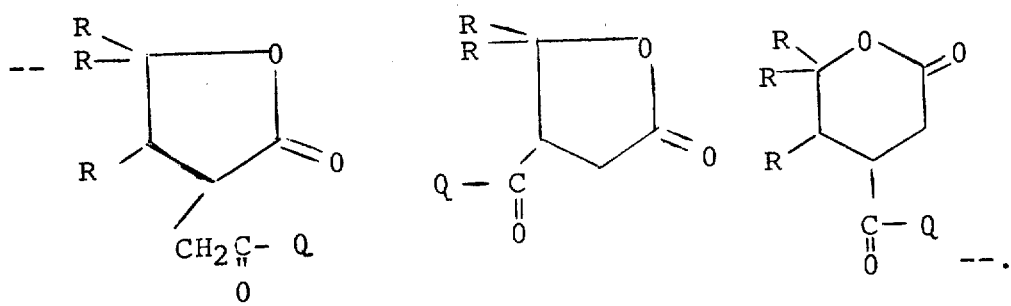

--.

Column 20, line 43 before "about" insert --between--;

line 56 before "said" insert --wherein n is 1 to 3,--.

Column 22, line 38 before "about" insert --between--;

line 51, before "said" insert --wherein n is 1 to 3,--.

Signed and Sealed this

Twenty-seventh Day of January 1981

[SEAL]

Attest:

RENE D. TEGTMEYER

Attesting Officer   Acting Commissioner of Patents and Trademarks